United States Patent [19]
Johnson

[11] Patent Number: 5,957,836
[45] Date of Patent: Sep. 28, 1999

[54] ROTATABLE RETRACTOR

[76] Inventor: Lanny L. Johnson, 2950 E. Mount Hope Rd., Okemos, Mich. 48864

[21] Appl. No.: 09/173,557

[22] Filed: Oct. 16, 1998

[51] Int. Cl.$^6$ .................................................. A61B 17/00
[52] U.S. Cl. ........................................................ 600/235
[58] Field of Search ................................. 600/201, 208, 600/209, 210, 235; 606/88, 90, 53, 54, 57; 433/148, 149

[56] References Cited

U.S. PATENT DOCUMENTS 5,217,463   6/1993   Mikhail ...................................... 606/88

FOREIGN PATENT DOCUMENTS 4307248   9/1994   Germany ................................ 433/148

OTHER PUBLICATIONS

Taylor, G. Mosser, "Simple Retractor for Spinal Surgery", College of Medical Evangelists, Los Angeles, vol. 28, No. 1, Jan. 1946.

*Primary Examiner*—Jeffrey A. Smith
*Attorney, Agent, or Firm*—Pillsbury Madison & Sutro LLP

[57] ABSTRACT

A rotatable retractor instrument for expanding a body joint is disclosed. A flattened portion is provided at the distal end of the instrument. With the flattened portion inserted within the joint, rotation of a handle at the instrument's proximal end spreads the joint.

2 Claims, 1 Drawing Sheet

ROTATABLE RETRACTOR

BACKGROUND OF THE INVENTION

1. Field of the Invention

The present invention relates to a surgical instrument for spreading a body joint.

2. Prior Art

It is customary to harvest cartilage tissue for pathological analysis or cell reproduction. This involves harvesting cartilage tissue from a patient and processing the tissue in a laboratory to grow a culture. If the cultured cells are then implanted in the patient, two invasions of the patient's body have occurred, each requiring general anesthesia.

It has been recognized that cartilage is available from a synovial joint that is expendable, e.g., the proximal fibular tibial joint. Typically, when harvesting cartilage from such a joint, the joint is sacrificed by being completely opened during the harvesting procedure.

SUMMARY OF THE INVENTION

The present invention relates to an instrument which permits access to an expandable joint without sacrificing it. By using this instrument, cartilage can be harvested on an outpatient basis in a procedure requiring only local anesthesia. The invention comprises a rod having a flattened portion at its distal end and a handle at its proximal end. The distal end of the instrument is inserted within the joint and is rotated so as to expand the joint.

BRIEF DESCRIPTION OF THE DRAWINGS

The invention will be described in greater detail with respect to the accompanying drawings wherein.

DETAILED DESCRIPTION OF A PREFERRED EMBODIMENT OF THE INVENTION

Figure 1:
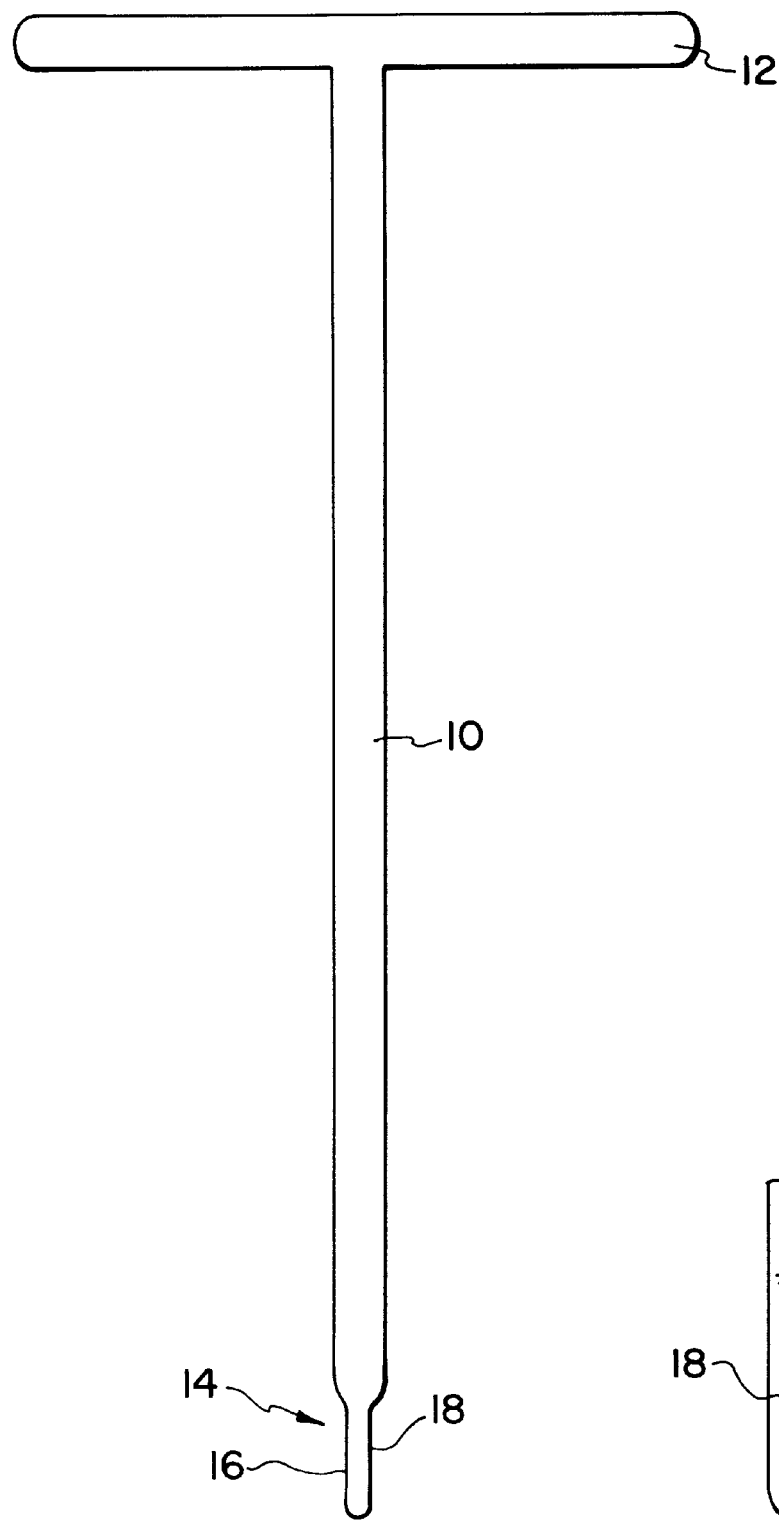
FIG. 1 is a side elevational view of a preferred embodiment of the invention.
Figure 2:
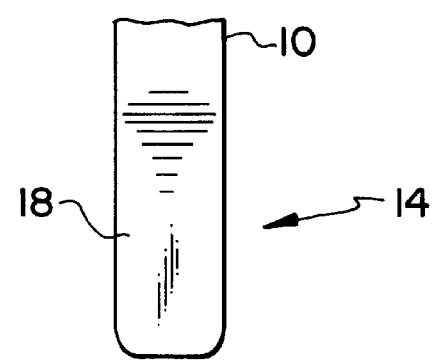
FIG. 2 is an enlarged end elevational view of a distal end portion of the embodiment shown in FIG. 1.

Referring to the drawings, the rotatable retractor according to the invention comprises a rod 10 having a handle 12 at its proximal end and a flattened portion 14 at its distal end. Portion 14 includes parallel surfaces 16 and 18 which are rounded at their side edges and distal ends to form a retractor which is blunted at its distal end. For use in expanding a proximal fibular tibial joint, the typical width of portion 14 is in the order of 5–10 mm., and its thickness is approximately 3 mm. For other joints, corresponding dimensions are dictated by size of the joint and how much it is to be expanded by the retractor.

In use, a short skin and subcutaneous incision over the anterior surface of the joint is made so as to expose, but not completely open, the joint. A first retractor is placed in the joint with surfaces 16 and 18 paralleling the joint, and a second retractor is placed in the joint with a similar orientation but proximal to the first retractor. The handles 12 of the retractors are rotated so as to move surfaces 16 and 18 substantially perpendicular to the length of the joint space thereby spreading the joint. The retractors remain so oriented by the force of the expandable joint opening when it is being spread. When the retractors are so positioned, access to the joint is obtained whereby cartilage can be harvested from it.

When harvesting of cartilage is completed, the handles of the retractors are rotated so as to move surfaces 16 and 18 in line with the joint, and they are withdrawn. The joint thereby contracts to its normal condition.

What is claimed is:

1. A rotatable retractor instrument for expanding a body joint, comprising:
   a rod;
   a handle located at a proximal end of the rod;
   a flattened end portion located at a distal end of the rod, said end portion including a pair of parallel surfaces, spaced from one another by a distance which permits the end portion to be inserted within said joint, and having widths greater than the distance between said surfaces whereby when said handle is rotated with the end portion inserted within the joint, said joint is expanded.

2. A rotatable retractor instrument according to claim 1, wherein distal edges of the end portion are rounded to blunt the end portion at a distal end thereof.

* * * * *